(12) United States Patent
Mankodi et al.

(10) Patent No.: US 11,191,448 B2
(45) Date of Patent: Dec. 7, 2021

(54) DYNAMIC STARTING RATE FOR GUIDED BREATHING

(71) Applicant: BOSE CORPORATION, Framingham, MA (US)

(72) Inventors: Harsh A. Mankodi, Brighton, MA (US); Chia-Chun Hsu, Brighton, MA (US); David Rolland Crist, Watertown, MA (US); Kathleen Elizabeth Kremer, Southborough, MA (US)

(73) Assignee: BOSE CORPORATION, Framingham, MA (US)

( * ) Notice: Subject to any disclaimer, the term of this patent is extended or adjusted under 35 U.S.C. 154(b) by 229 days.

(21) Appl. No.: 16/434,451

(22) Filed: Jun. 7, 2019

(65) Prior Publication Data

US 2020/0383605 A1 Dec. 10, 2020

(51) Int. Cl.
*A61B 5/08* (2006.01)
*A61M 21/02* (2006.01)
*G16H 20/30* (2018.01)
*A61M 21/00* (2006.01)

(52) U.S. Cl.
CPC .......... *A61B 5/0816* (2013.01); *A61M 21/02* (2013.01); *A61M 2021/0027* (2013.01); *G16H 20/30* (2018.01)

(58) Field of Classification Search
CPC . A61B 5/0816; A61B 5/486; A61M 21/00–02
See application file for complete search history.

(56) References Cited

U.S. PATENT DOCUMENTS

| 2006/0064037 A1* | 3/2006 | Shalon | G16H 20/60 |
| | | | 600/586 |
| 2008/0269629 A1* | 10/2008 | Reiner | A61B 7/02 |
| | | | 600/544 |
| 2009/0024047 A1 | 1/2009 | Shipley et al. | |
| 2014/0316192 A1* | 10/2014 | de Zambotti | A61B 5/0205 |
| | | | 600/28 |
| 2018/0078735 A1 | 3/2018 | Dalgleish et al. | |
| 2018/0110461 A1* | 4/2018 | Yamaki | A61B 5/11 |
| 2019/0030278 A1 | 1/2019 | Kremer et al. | |

FOREIGN PATENT DOCUMENTS

GB 2567678 A 4/2019

OTHER PUBLICATIONS

International Search Report and Written Opinion for International Application No. PCT/US2020/036382 dated Sep. 14, 2020.

* cited by examiner

*Primary Examiner* — Thaddeus B Cox
(74) *Attorney, Agent, or Firm* — Patterson + Sheridan, LLP

(57) ABSTRACT

Aspects of the present disclosure provide methods, apparatuses, and systems for dynamic starting rates for guided breathing. According to an aspect, a user's initial breathing metric is determined. A multiplier is then determined, where the multiplier varies as a function of the initial breathing metric within a range. The level of intensity of the multiplier may vary, and may be a dynamic feature based on the determination of the user's initial breathing metric. Once the multiplier is determined, the multiplier is applied to the user's initial breathing metric to determine a starting breathing metric for guided breathing. The starting breathing metric is slower than or equal to the user's initial breathing metric.

10 Claims, 5 Drawing Sheets

| MEASURED BrPM | ADJUSTED STARTING BrPM | | | |
|---|---|---|---|---|
| | DYNAMIC | | | FIXED |
| | MILD 502 | MEDIUM 504 | STRONG 506 | 1.1x |
| 20 | 15.9 | 15.1 | 14.4 | 18.2 |
| 18 | 14.5 | 13.9 | 13.3 | 16.4 |
| 16 | 13.2 | 12.6 | 12.1 | 14.5 |
| 14 | 11.8 | 11.4 | 11 | 12.7 |
| 12 | 10.5 | 10.2 | 9.9 | 10.9 |
| 10 | 9.2 | 9 | 8.9 | 9.1 |
| 8 | 8 | 8 | 8 | 7.3 |

DYNAMIC STARTING RATE FOR GUIDED BREATHING

FIELD

Aspects of the present disclosure generally relate to methods, apparatuses, and systems for dynamic starting rates for guided breathing.

BACKGROUND

Utilizing guided breathing to regulate a user or subject's breathing rate, or amount of breaths taken per minute, can be beneficial in a number of health fields. For example, guided breathing can be used in several clinical applications, potentially leading to more effective or quicker treatments of conditions, including: asthma, stress, anxiety, insomnia, panic disorder, recurrent abdominal pain, chronic obstructive pulmonary disease, chronic hyperventilation, hypertension, and congestive heart failure, among others. Guided breathing may also be utilized to assist people in falling asleep and for meditation or relaxation purposes.

Many guided breathing exercises start at a rate that matches a user's current measured breathing rate. However, many users find starting at their current measured breathing rate to be uncomfortable. When the starting breathing rate is uncomfortable for a user, the guided breathing exercise is difficult to follow, which may result in the overall guided breathing exercise being unpleasant. Therefore, there is a need for a starting breathing metric for guided breathing exercises that is more comfortable for users to follow.

SUMMARY

Aspects of the present disclosure provide methods, apparatuses, and systems for dynamic starting rates for guided breathing. According to an aspect, a user's initial breathing metric is determined. A multiplier is then determined, where the multiplier varies as a function of the initial breathing metric within a range. The level of intensity of the multiplier may vary, and may be a dynamic feature based on the determination of the user's initial breathing metric. Once the multiplier is determined, the multiplier is applied to the user's initial breathing metric to determine a starting breathing metric for guided breathing. The starting breathing metric is slower than or equal to the user's initial breathing metric.

In an aspect, a method for determining a starting breathing metric for guided breathing comprises determining an initial breathing metric of a user, determining a multiplier, wherein the multiplier varies as a function of the initial breathing metric within a range, and applying the multiplier to the initial breathing metric of the user.

The breathing metric may comprise one of a breaths per minute rate of the user or a breathing period of the user. Determining the initial breathing metric of the user may comprise measuring a current breathing rate of the user. The breathing metric may comprise a breathing period of the user, and when the initial breathing metric of the user is determined to be between a first value and a second value higher than the first value, the multiplier varies in a linearly decreasing manner, and when the initial breathing metric of the user is determined to be between the second value and a third value higher than the second value, the multiplier is constant. The range may be between about 2 seconds and about 7.5 seconds. The multiplier may vary between about 1 and about 1.3. When the breathing metric comprises a breaths per minute rate of the user, the multiplier may be lower when the initial breathing metric of the user is higher as compared to when the initial breathing metric is lower. When the breathing metric comprises a breathing period of the user, the multiplier may be higher when the initial breathing metric of the user is lower as compared to when the initial breathing metric is higher.

Determining the initial breathing metric of the user comprises measuring a current breathing rate of the user and converting the measured current breathing rate of the user to a breathing period, determining the multiplier comprises determining the multiplier based on the breathing period of the user, and applying the multiplier to the initial breathing metric of the user comprises applying the ratio to the breathing period of the user to provide a modified breathing period. The modified breathing period may be used as the starting breathing metric for the guided breathing, and the starting breathing metric may be in units of breaths per minute rate or period of a breath in seconds.

In yet another aspect, a stimulus output system comprises at least one transducer configured to output a guiding stimulus to a user, and a processor, the processor configured to determine a starting breathing metric for the guiding stimulus by determining a starting breathing metric for guided breathing comprises determining an initial breathing metric of a user, determining a multiplier, wherein the multiplier varies as a function of the initial breathing metric within a range, and applying the multiplier to the initial breathing metric of the user.

The breathing metric may comprise one of a breaths per minute rate of the user or a breathing period of the user. Determining the initial breathing metric of the user may comprise measuring a current breathing rate of the user. The breathing metric may comprise a breathing period of the user, and when the initial breathing metric of the user is determined to be between a first value and a second value higher than the first value, the multiplier varies in a linearly decreasing manner, and when the initial breathing metric of the user is determined to be between the second value and a third value higher than the second value, the multiplier is constant. The range may be between about 2 seconds and about 7.5 seconds. The multiplier may vary between about 1 and about 1.3. When the breathing metric comprises a breaths per minute rate of the user, the multiplier may be lower when the initial breathing metric of the user is higher as compared to when the initial breathing metric is lower. When the breathing metric comprises a breathing period of the user, the multiplier may be higher when the initial breathing metric of the user is lower as compared to when the initial breathing metric is higher. The initial breathing metric of the user may be estimated using a biometric sensor.

Determining the initial breathing metric of the user comprises measuring a current breathing rate of the user and converting the measured current breathing rate of the user to a breathing period, determining the multiplier comprises determining the multiplier based on the breathing period of the user, and applying the multiplier to the initial breathing metric of the user comprises applying the ratio to the breathing period of the user to provide a modified breathing period. The modified breathing period may be used as the starting breathing metric for the guided breathing, and the starting breathing metric may be in units of breaths per minute rate or period of a breath in seconds.

In another aspect, a wearable audio device comprises at least one speaker configured to output a guiding stimulus to a user, and a processor, the processor configured to determine a starting breathing metric for the guiding stimulus by determining a starting breathing metric for guided breathing comprises determining an initial breathing metric of a user, determining a multiplier, wherein the multiplier varies as a function of the initial breathing metric within a range, and applying the multiplier to the initial breathing metric of the user.

The breathing metric may comprise one of a breaths per minute rate of the user or a breathing period of the user. Determining the initial breathing metric of the user may comprise measuring a current breathing rate of the user. The breathing metric may comprise a breathing period of the user, and when the initial breathing metric of the user is determined to be between a first value and a second value higher than the first value, the multiplier varies in a linearly decreasing manner, and when the initial breathing metric of the user is determined to be between the second value and a third value higher than the second value, the multiplier is constant. The range may be between about 2 seconds and about 7.5 seconds. The multiplier may vary between about 1 and about 1.3. When the breathing metric comprises a breaths per minute rate of the user, the multiplier may be lower when the initial breathing metric of the user is higher as compared to when the initial breathing metric is lower. When the breathing metric comprises a breathing period of the user, the multiplier may be higher when the initial breathing metric of the user is lower as compared to when the initial breathing metric is higher. The initial breathing metric of the user may be estimated using a biometric sensor.

Determining the initial breathing metric of the user comprises measuring a current breathing rate of the user and converting the measured current breathing rate of the user to a breathing period, determining the multiplier comprises determining the multiplier based on the breathing period of the user, and applying the multiplier to the initial breathing metric of the user comprises applying the ratio to the breathing period of the user to provide a modified breathing period. The modified breathing period may be used as the starting breathing metric for the guided breathing, and the starting breathing metric may be in units of breaths per minute rate or period of a breath in seconds.

All examples and features mentioned herein can be combined in any technically possible manner.

DETAILED DESCRIPTION

Figure 1:
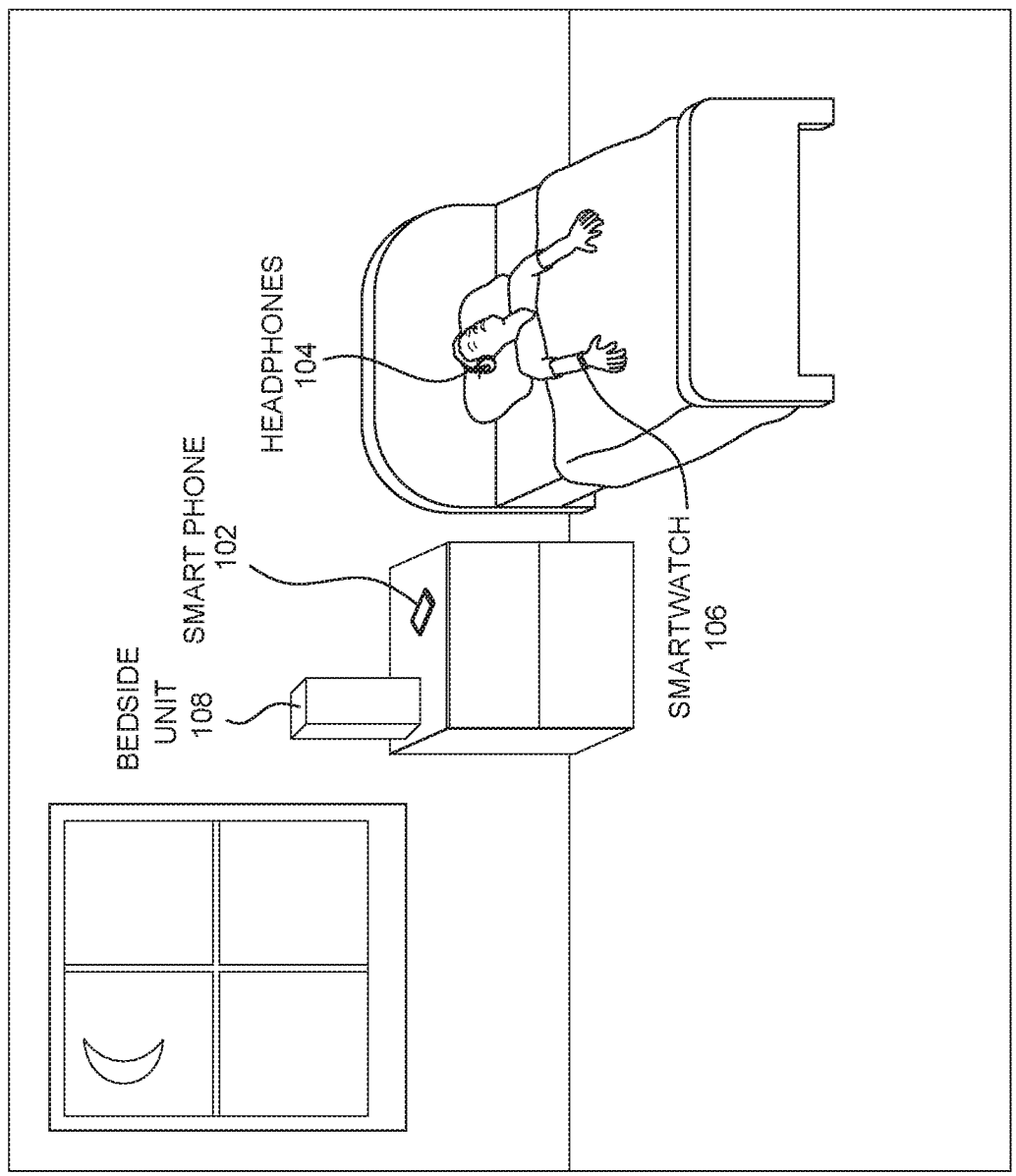
FIG. 1 illustrates an example stimulus output system in a sleeping environment.

FIG. 1 illustrates an example stimulus output system 100 in a sleeping environment, according to an aspect. The stimulus output system 100 may be used to determine a dynamic starting breathing metric, and to non-linearly alter a guiding stimulus from the dynamic starting breathing metric to a target breathing metric for non-linear guided breathing. The stimulus output system 100 may be an audio system.

The stimulus output system 100 includes headphones 104 and a smartwatch 106, which are shown as being worn by a subject or user. A headphone 104 refers to a device that fits around, on, or in an ear and that radiates acoustic energy into the ear canal. Headphones 104 are sometimes referred to as earphones, earpieces, headsets, earbuds, or sport headphones, and can be wired or wireless. The headphones 104 may comprise one or more of: a processing unit, a transceiver, one or more biosensors, one or more speakers, one or more systems configured to output any combination of haptics, lighting and audio, and one or more microphones. The headphones 104 may comprise an interface configured to receive input from a subject or user. A smartwatch 106 may be any type of wearable computer designed to be worn on a wrist of a subject or user, such as a fitness tracker. The smartwatch 106 may comprise one or more of: a processing unit, a transceiver, one or more biosensors, one or more speakers, one or more haptic systems, and one or more microphones. The smartwatch 106 may comprise an interface configured to receive input from a subject or user.

The stimulus output system 100 further includes a bedside unit 108 and a smartphone 102. The smartphone 102 may be a mobile phone, tablet, phablet, or laptop computer. The smartphone 102 may comprise one or more of: a processing unit, a transceiver, one or more biosensors, one or more speakers, one or more haptic systems, one or more light sources, and one or more microphones. The smartphone 102 may comprise an interface configured to receive input from a subject or user. The bedside unit 108 may be a stationary smart device, such as a smart speaker. The bedside unit 108 may have any shape and size capable of fitting on a surface in the sleeping environment, such as a dresser, desk, or night table. The bedside unit 108 may comprise one or more of: a processing unit, a transceiver, one or more biosensors, one or more speakers, one or more haptic systems, one or more light sources, and one or more microphones. In one embodiment, the bedside unit 108 comprises one or more contactless biosensors, such as a radio frequency (RF) sensor, a radar sensor, or an under-bed accelerometer and/or microphone. The bedside unit 108 may comprise an interface configured to receive input from a subject or user.

The headphones 104, the smartwatch 106, the bedside unit 108, and the smartphone 102 may each include any wired or wireless communication means suitable for use with any other device 102-108 disposed in the sleeping environment, such as WiFi, Bluetooth, Near Field Communications (NFC), USB, micro USB, or any suitable wired or wireless communications technologies known to one of ordinary skill in the art. For example, the headphones 104 may comprise one or more speakers while the bedside unit 108 comprises one or more biosensors in communication with the one or more speakers of the headphones 104. Furthermore, the stimulus output system 100 may include one or more of the devices 102-108, and is not required to include each device 102-108 shown. Thus, each device 102-108 in the stimulus output system 100 may be optionally included, and only one device 102-108 is needed for guiding breathing exercises and for determining a starting breathing metric for such guided breathing exercises.

The devices 102-108 of the stimulus output system 100, either alone or in combination, are configured to: determine a starting breathing metric for guided breathing by determining an initial breathing metric of a user, determining a multiplier, wherein the multiplier varies as a function of the initial breathing metric within a range, and applying the multiplier to the initial breathing metric of the user. The stimulus output system 100 may output a guided breathing stimulus to a user in the form of audio, haptics, lights, etc.

Figure 2:
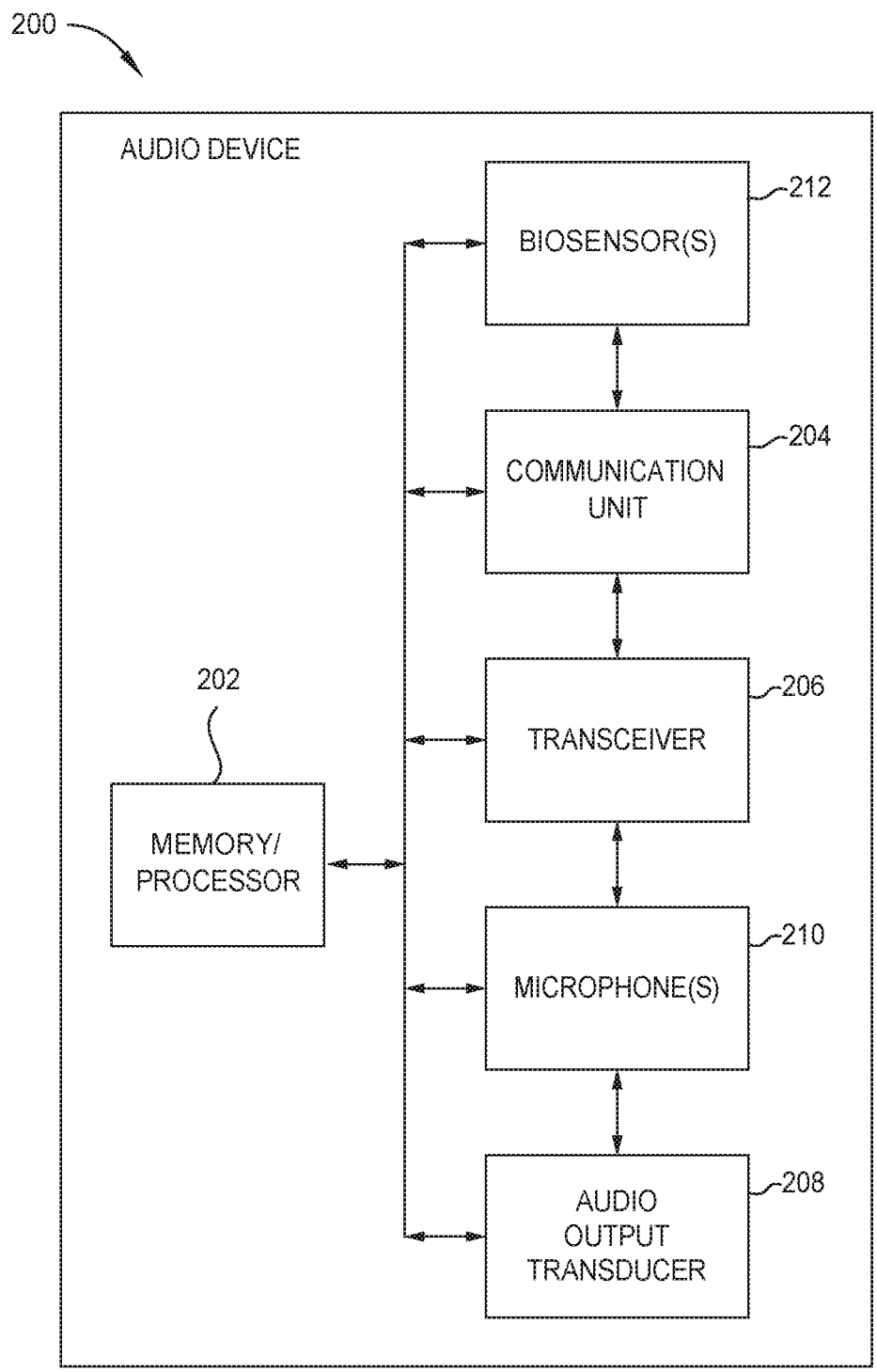
FIG. 2 illustrates example components of a stimulus output device.

FIG. 2 illustrates example components of a stimulus output device 200, in accordance with certain aspects of the present disclosure. According to an example, the stimulus output device 200 is a wireless wearable audio device. The stimulus output device 200 may be an audio output device. The stimulus output device 200 may be used in a stimulus output system, such as the stimulus output system 100 of FIG. 1. For instance, the stimulus output device 200 may be any device 102-108 in the stimulus output system 100 of FIG. 1. In one example, the stimulus output device 200 is the headphones 104 of FIG. 1. In another example, the stimulus output device 200 is the bedside unit 108 of FIG. 1. The stimulus output device 200 may be used to determine a dynamic starting breathing metric, and to non-linearly alter a guiding stimulus from the dynamic starting breathing metric to a target breathing metric for non-linear guided breathing.

The stimulus output device 200 includes a memory and processor 202, communication unit 204, a transceiver 206, a biosensor 212, and an audio output transducer or speaker 208. The memory may include Read Only Memory (ROM), a Random Access Memory (RAM), and/or a flash ROM. The memory stores program code for controlling the memory and processor 202. The memory and processor 202 control the operations of the stimulus output device 200. Any or all of the components in FIG. 2 may be combined into multi-function components.

The processor 202 controls the general operation of the stimulus output device 200. For example, the processor 202 performs process and control for audio and/or data communication. The processor 202 is configured to determine a starting breathing metric for guided breathing by determining an initial breathing metric of a user, determining a multiplier, wherein the multiplier varies as a function of the initial breathing metric within a range, and applying the multiplier to the initial breathing metric of the user. The processor 202 is configured to measure, receive, calculate, or detect at least one biosignal parameter of the subject. In combination with the audio output transducer 208, the processor 202 is configured to output a guiding stimulus. The processor 202 is further configured to alter the guiding stimulus. The processor 202 may be further configured to receive input from a subject or user, such as input regarding an initial breathing metric and a final breathing metric. In at least one example, the processor 202 is disposed on another device in an audio system, such as a smartphone, and is in communication with the stimulus output device 200.

The communication unit 204 facilitates a wireless connection with one or more other wireless devices, such as with other devices in an audio system. For example, the communication unit 204 may include one or more wireless protocol engines such as a Bluetooth engine. While Bluetooth is used as an example protocol, other communication protocols may also be used. Some examples include Bluetooth Low Energy (BLE), NFC, IEEE 802.11, WiFi, or other local area network (LAN) or personal area network (PAN) protocols. The stimulus output device 200 may receive audio files wirelessly via the communication unit 204. Additionally or alternatively, the communication unit 204 may receive information associated with a subject's biosignal parameters, obtained via a contactless sensor. Examples of contactless sensors include a radio frequency (RF) sensor, a radar sensor, or an under-bed accelerometer.

The transceiver 206 transmits and receives information via one or more antennae to exchange information with one or more other wireless devices. The transceiver 206 may be used to communicate with other devices in an audio system, such as a bedside unit, a smartphone, and/or a smartwatch. The transceiver 206 is not necessarily a distinct component.

The stimulus output device 200 includes the audio output transducer 208, which may be also known as a driver or speaker. In some examples, more than one output transducer 208 is used. The transducer 208 (that may be part of a microphone) converts electrical signals into sound and converts sound into electrical signals. The transducer 208 is configured to output a guiding stimulus to a user or subject. The transducer 208 outputs audio signals, including adjusted audio signals in an effort to regulate a user's breathing. For example, the transducer 208 may be configured to adjust audio signals in response to a subject's biosignal parameters. In at least one example, the transducer 208 is disposed on another device in an audio system, such as a bedside unit, and is in communication with the stimulus output device 200.

The stimulus output device 200 optionally includes one or more microphones 210. In an aspect, the microphones 210 are used to convert noises into electrical signals. In at least one example, one or more microphones 210 are disposed on another device in an audio system, such as a bedside unit, and are in communication with the stimulus output device 200. The microphone 210 may be used to approximate or measure a user's breathing metric, such as breaths per minute rate.

The stimulus output device 200 optionally includes one or more biosensors 212 used to determine, sense, measure, monitor, or calculate a biosignal parameter of a subject wearing the stimulus output device 200.

According to an aspect when the stimulus output device 200 is headphones, only one earpiece (ear tip, ear cup) of the stimulus output device 200 includes the biosensor 212. In an aspect, neither earpiece includes a biosensor 212. Instead, a biosensor 212, not on the stimulus output device 200, may remotely detect a biosignal parameter of the subject. In an example, the biosensor 212 detects a subject's heartrate or heart rate variability (HRV) with a sensor disposed on the wrist, such as by utilizing a smartwatch. In an example, the biosensor 212 may be a contactless biosensor. The contactless biosensor is configured to report detected biosignal parameters to the processor 202, for example, via the communication unit 204. In at least one example, the biosensor 212 is disposed on another device in an audio system, such as a smartwatch, and is in communication with the stimulus output device 200.

FIG. 2 illustrates communication between certain modules of an example stimulus output device 200; however, aspects of the disclosure are not limited to the specific illustrated example. According to aspects, any module 202-212 is configured to communicate with any other module in the stimulus output device 200. In one example, all modules 202-212 are connected to and communicate with each other. The stimulus output device 200 may output a guided breathing stimulus to a user in the form of audio, haptics, lights, etc.

Figure 3:
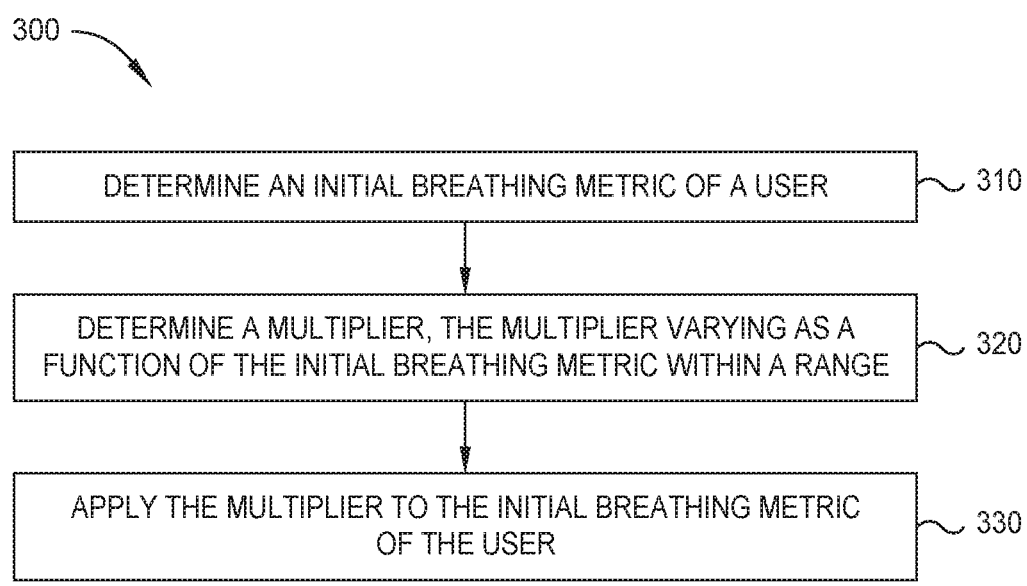
FIG. 3 illustrates an example method for determining a starting breathing metric for guided breathing.
Figure 4:
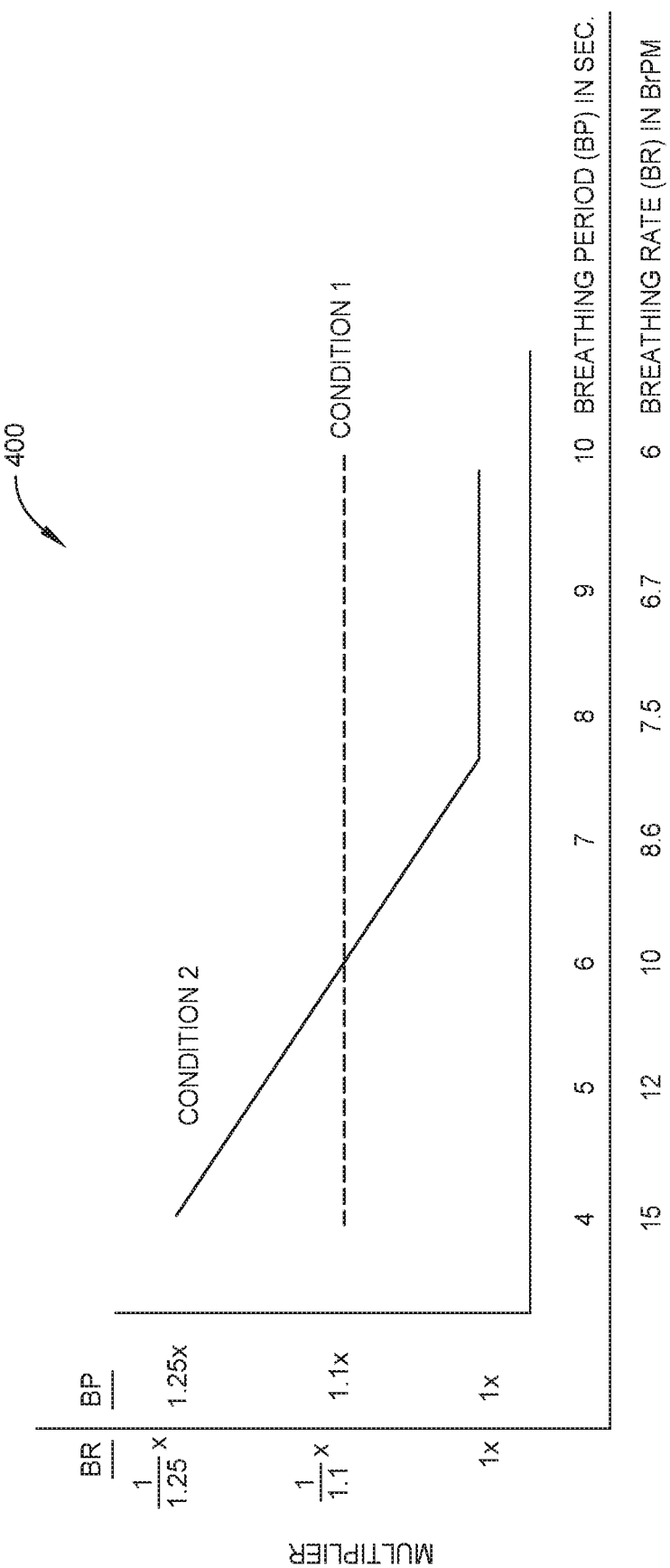
FIG. 4 illustrates an example diagram for determining a multiplier utilized in determining the starting breathing metric.

FIG. 3 illustrates an example method 300 for determining a dynamic starting breathing metric for guided breathing. FIG. 4 illustrates an exemplary diagram 400 that may be utilized to determine a multiplier to apply to a breathing metric to determine a dynamic starting breathing metric for guided breathing. A breathing metric may comprise one of a breathing rate or a breathing period. A breathing period is an amount of time in seconds from a beginning of one inhale to an end of a next exhale. A breathing rate, or breaths per minute rate (BrPM) (e.g. breath rate per minute or breathing rate per minute), is the amount or number of breaths a subject takes in one minute. The terms "breaths per minute rate", "breath rate per minute", "breathing rate", and "breathing rate per minute" as used herein may be used interchangeably. The method 300 and the diagram 400 may each individually be utilized with the stimulus output system 100 of FIG. 1 and/or the stimulus output device 200 of FIG. 2.

At 310, an initial breathing metric of a user is determined. The initial breathing metric may be determined by measuring the current breathing rate or breathing period of the user. In one embodiment, a biometric sensor, such as the biometric sensor 212 of FIG. 2, may be used to estimate or measure the breathing rate of the user. In other embodiments, the breathing metric may be determined based on historical data, demographic data, preference data, or the like. For example, a user's breathing rate or breathing period may be measured using a biometric sensor every day for one or more days around the same time each day to gather historical data. Based on the collected historical data, the user's breathing metric may be determined or estimated, such as by averaging the breathing metrics collected. As another example, a user may input their demographic data, such as race, height, weight, known medical conditions, diet, etc. into an interface. The demographic data may then be analyzed to approximate the user's initial breathing metric. If the breathing metric is determined in units of breaths per minute rate (i.e., breathing rate), the breathing metric may be converted to units of period of a breath in seconds (i.e., breathing period) prior to continuing to 320.

At 320, a multiplier is determined, the multiplier varying as a function of the initial breathing metric within a range. The multiplier may vary linearly as a function of breaths per minute rate such that the higher the user's initial breathing rate is, the higher the multiplier. The range for the varying function of the multiplier may be between about a 2 second period to about a 7.5 second period.

FIG. 4 illustrates an exemplary diagram 400 that may be utilized to determine the multiplier. The diagram 400 may be used as a look up table and illustrates two conditions for determining the multiplier. While FIG. 4 shows the highest multiplier being 1.25, the multiplier may be higher, such as 1.3, as described below in FIGS. 5A-5B. The multiplier may be a ratio of the user's initial breathing metric divided by a preselected starting breathing metric found to be a comfortable starting breathing metric for the user. While the diagram 400 illustrates multipliers for both a breathing period (BP) and a breathing rate (BR) along the y-axis, only one unit of multiplier is needed. The multiplier may be determined for either a breathing rate or a breathing period of a user, regardless of the unit of the multiplier.

Under condition 1 in the diagram 400, a user's initial breathing metric is multiplied by the same multiplier regardless of what the user's initial breathing metric is. As shown in the diagram 400, the multiplier under condition 1 is always 1.1 for breathing periods (i.e., about 0.908 for breathing rates). Similarly, while not shown on the diagram 400, one BrPM may be subtracted from the user's initial breathing metric, or one second may be added, regardless of what the user's initial breathing metric is.

Under condition 2 in the diagram 400, the multiplier varies linearly as a function of breaths per minute rate from a first value to a second value, and then becomes constant from the second value to a third value. For example, when the first value is about a 4 second period or higher and the second value is about an 8 second period, the multiplier varies in a decreasing linear manner. When the second value is about an 8 second period and the third value is about a 10 second period, the multiplier is constant at 1. When the multiplier varies in a decreasing linear manner, the higher the user's initial breathing rate is, the lower the multiplier. Similarly, when the multiplier varies in a decreasing linear manner, the lower the user's initial breathing period is, the higher the multiplier. For example, if a user's initial breathing metric is about 6 seconds, a multiplier of 1.1 is selected (i.e., a multiplier of about 0.908 for a corresponding breathing rate of 10 BrPM). However, when a user's initial breathing metric is about 4 seconds, a multiplier of about 1.25 is selected (i.e., a multiplier of about 0.8 for a corresponding breathing rate of 15 BrPM).

At 330, the multiplier determined at 320 is applied to the initial breathing metric of the user to determine a starting breathing metric for guided breathing. The starting breathing metric is slower than or equal to the user's initial breathing metric. Under condition 1 in the diagram 400, if a user's initial breathing metric is determined to be a 5 second period, the user's determined starting metric would be a 5.5 second period, or about 10.9 breaths per minute. Under condition 2 in the diagram 400, if a user's initial breathing metric is determined to be a 5 second period, the user's determined starting metric would be a 5.875 second period, or about 10.21 breaths per minute. In one aspect, the starting breathing metric is bound such that the starting breathing rate never starts lower than about 10 seconds (i.e., 6 BrPM) and never starts higher than about 4 seconds (i.e., 15 BrPM). Once the starting breathing metric is determined, it may be used as the breathing metric to start a guided breathing exercise as the starting breathing metric for a guided breathing stimulus.

While referred to as a multiplier, the multiplier may be applied to the initial breathing metric through any mathematical operation or function, including but not limited to, addition, subtraction, multiplication, or division. In one example, the initial breathing metric in terms of breathing rate per minute may be subtracted by 1 for all values of breathing rate per minute. In another example, if the multiplier is determined to be 1.25 in 320, the initial breathing metric of the user may be multiplied by 1.25 if the initial breathing metric is in units of a breathing period, or the initial breathing metric may be divided by 1.25 if the initial breathing metric is in units of breaths per minute rate. Conversely, if the multiplier is determined to be 0.8 in 320, the initial breathing metric of the user may be divided by 0.8 if the initial breathing metric is in units of a breathing period, or the initial breathing metric may be multiplied by 0.8 if the initial breathing metric is in units of breaths per minute rate. Thus, regardless of the unit of the multiplier, the multiplier may be applied to both a breathing rate and a breathing period of a user.

Figures 5A, 5B:
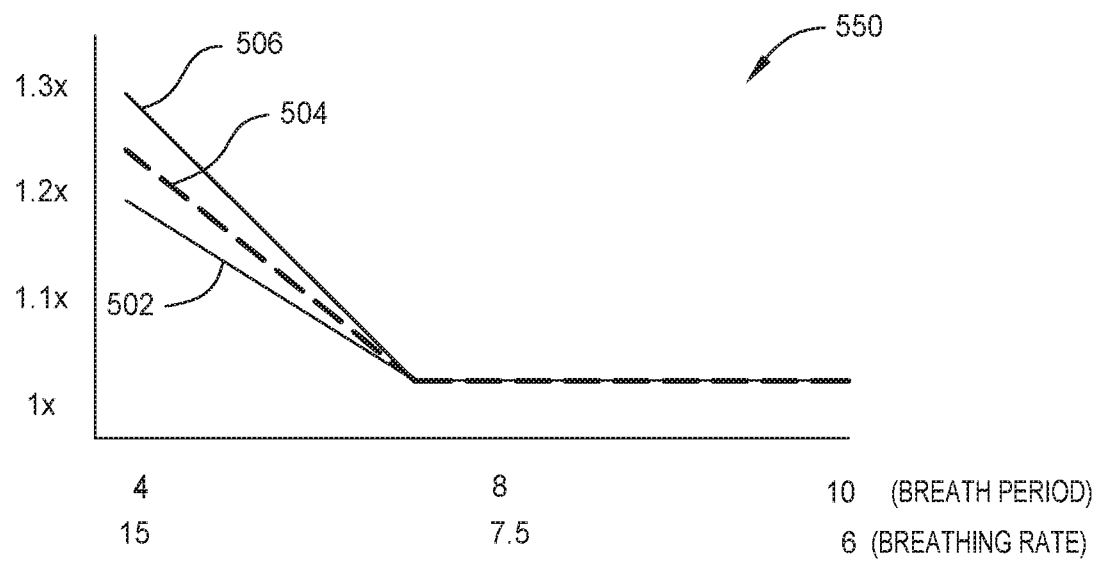
FIGS. 5A-5B illustrate an example chart and corresponding diagram for selecting an intensity level of a multiplier.

FIG. 5A illustrates an exemplary chart 500 for various levels of intensities of multipliers, and FIG. 5B illustrates a corresponding diagram 550. The chart 500 and the diagram 550 may be utilized with the stimulus output system 100 of FIG. 1, the stimulus output device 200 of FIG. 2, and or the method 300 of FIG. 3. The chart 500 and the diagram 550 illustrate various levels of intensities or severities for determining multipliers for condition 2 described above in 320. As shown in the chart 500, various intensities or severities, such as mild, medium, and strong, may be selected for determining the rate at which the multiplier may decreasingly vary (i.e., the slope of the line for condition 2). The mild level 502 determines a lower, or weaker, intensity to apply to a user's initial breathing metric while the strong level 506 determines a higher, or steeper, intensity. The chart 500 further illustrates a fixed multiplier of 1.1, relating to condition 1 above, for comparison. While the chart 500 is shown in units of breathing rate, the chart 500 may be in units of breathing period.

In the chart 500, the mild level 502 starts at a multiplier of about 1.25 for an initial breathing rate of about 20 breaths per minute, the medium level 504 starts at a multiplier of about 1.23 for an initial breathing rate of about 20 breaths per minute, and the strong level 506 starts at a multiplier of about 1.39 for an initial breathing rate of about 20 breaths per minute. The diagram 550 illustrates each of the levels of intensities starting at a high breathing rate of about 15 breaths per minute. In the diagram 550, the mild level 502 starts at a multiplier of about 1.185 for an initial breathing rate of about 125 breaths per minute, the medium level 504 starts at a multiplier of about 1.25 for an initial breathing rate of about 15 breaths per minute, and the strong level 506 starts at a multiplier of about 1.3 for an initial breathing rate of about 15 breaths per minute. Like in the diagram 400, if a user's initial breathing period is determined to be about 8 or 9 breaths per minute, the multiplier no longer decreases linearly, and is instead constant at 1.

The level of intensity may be user selected or may be predetermined. In one embodiment, the level of intensity is a dynamic feature that is selected based on the user's initial breathing metric. For instance, the lower the user's initial breathing metric, the lower the level of intensity of the multiplier, and the higher the user's initial breathing metric, the higher the level of intensity of the multiplier. For example, if a user's initial breathing metric is determined to be about 8 BrPM to about 11 BrPM, the mild intensity may be selected. Similarly, if the user's initial breathing metric is determined to be about 12 BrPM to about 19 BrPM, the medium intensity may be selected. If the user's initial breathing metric is determined to be about 20 BrPM or higher, the strong intensity may be selected. If the user's initial breathing metric is determined to be about 8 BrPM of lower, the constant multiplier of 1 is selected.

By determining a starting breathing metric for guided breathing different from a user's current breathing metric, the guided breathing will start at a more comfortable pace, which may help the user reach a target breathing metric quicker. Additionally, by starting the guided breathing at a more comfortable pace, a user may be more encourage to complete the guided breathing, as the guided breathing will feel smoother than a guided breathing exercise started at the user's current breathing metric, helping the user reach their target breathing metric quicker. As such, the overall guided breathing experience will be more efficient and beneficial to a user, as the guided breathing experience will be more comfortable and easier for the user to follow.

Aspects of the present disclosure provide methods, apparatuses, and systems for dynamic starting rates for guided breathing. According to aspects, the audio device or system described herein is also configured to non-linearly alter a guiding stimulus with a non-linear breath rate per minute or breaths per minute rate sequence to align with a final or target breathing period, as described in U.S. Patent Application Ser. No. 62/789,343 entitled "Non-Linear Breath Entrainment," filed on Jan. 7, 2019, which is hereby incorporated by reference in its entirety.

In the preceding, reference is made to aspects presented in this disclosure. However, the scope of the present disclosure is not limited to specific described aspects. Aspects of the present disclosure may take the form of an entirely hardware embodiment, an entirely software embodiment (including firmware, resident software, micro-code, etc.) or an embodiment combining software and hardware aspects that may all generally be referred to herein as a "component," "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples of a computer readable storage medium include: an electrical connection having one or more wires, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the current context, a computer readable storage medium may be any tangible medium that can contain, or store a program.

The flowchart and block diagrams in the figures illustrate the architecture, functionality and operation of possible implementations of systems, methods and computer program products according to various aspects. In this regard, each block in the flowchart or block diagrams may represent a module, segment or portion of code, which comprises one or more executable instructions for implementing the specified logical function(s). In some implementations the functions noted in the block may occur out of the order noted in the figures. For example, two blocks shown in succession may, in fact, be executed substantially concurrently, or the blocks may sometimes be executed in the reverse order, depending upon the functionality involved. Each block of the block diagrams and/or flowchart illustrations, and combinations of blocks in the block diagrams and/or flowchart illustrations can be implemented by special-purpose hardware-based systems that perform the specified functions or acts, or combinations of special purpose hardware and computer instructions.

The invention claimed is:

1. A wearable audio device, comprising:
a processor, the processor configured to determine a starting breathing metric for a guiding stimulus by:
determining an initial breathing metric of a user; and
determining a multiplier, wherein the multiplier varies as a function of the initial breathing metric within a range and the function of the initial breathing metric varies based on the range; and
applying the multiplier to the initial breathing metric of the user to get a starting breathing metric; and
at least one speaker configured to use the starting breathing metric to output the guiding stimulus to a user.

2. The wearable audio device of claim 1, wherein the initial breathing metric comprises one of a breaths per minute rate of the user or a breathing period of the user.

3. The wearable audio device of claim 1, wherein determining the initial breathing metric of the user comprises measuring a current breathing rate of the user.

4. The wearable audio device of claim 1, wherein the initial breathing metric comprises a breathing period of the user, and wherein:

when the initial breathing metric of the user is determined to be between a first value and a second value higher than the first value, the multiplier varies in a linearly decreasing manner, and when the initial breathing metric of the user is determined to be between the second value and a third value higher than the second value, the multiplier is constant.

5. The wearable audio device of claim 1, wherein the range is between about 2 seconds and about 7.5 seconds.

6. The wearable audio device of claim 1, wherein the multiplier varies between about 1 and about 1.3.

7. The wearable audio device of claim 1, wherein:

when the initial breathing metric comprises a breaths per minute rate of the user, the multiplier is lower when the initial breathing metric of the user is higher as compared to when the initial breathing metric is lower, and when the initial breathing metric comprises a breathing period of the user, the multiplier is higher when the initial breathing metric of the user is lower as compared to when the initial breathing metric is higher.

8. The wearable audio device of claim 1, further comprising a biometric sensor, wherein the initial breathing metric of the user is estimated using the biometric sensor.

9. The wearable audio device of claim 1, wherein:

determining the initial breathing metric of the user comprises measuring a current breathing rate of the user and converting the measured current breathing rate of the user to a breathing period;

determining the multiplier comprises determining the multiplier based on the breathing period of the user; and applying the multiplier to the initial breathing metric of the user comprises applying the multiplier to the breathing period of the user to provide a modified breathing period.

10. The wearable audio device of claim 9, further comprising:

using the modified breathing period as the starting breathing metric for the guiding stimulus, wherein the starting breathing metric is in units of breaths per minute rate or period of a breath in seconds.

* * * * *